United States Patent [19]

Tayot

[11] 4,415,733
[45] Nov. 15, 1983

[54] GANGLIOSIDE DERIVATIVES, THEIR PREPARATION AND THEIR APPLICATION

[75] Inventor: Jean-Louis Tayot, Lyon la Ducherie, France

[73] Assignee: Societe Anonyme dite: Institut Merieux, Lyons, France

[21] Appl. No.: 244,312

[22] Filed: Mar. 16, 1981

[30] Foreign Application Priority Data

Mar. 17, 1980 [FR] France .............................. 80 05891

[51] Int. Cl.³ .............................................. C08B 37/00
[52] U.S. Cl. ........................................ 536/53; 536/55.1
[58] Field of Search ................................ 536/53, 55.1

[56] References Cited

U.S. PATENT DOCUMENTS 4,225,487 9/1980 Cuatrecasas ........................ 536/1.1

*Primary Examiner*—Alan Siegel
*Attorney, Agent, or Firm*—Cushman, Darby & Cushman

[57] ABSTRACT

This invention has for its object new ganglioside derivatives, their preparation and their application.

7 Claims, No Drawings

GANGLIOSIDE DERIVATIVES, THEIR PREPARATION AND THEIR APPLICATION

The role of gangliosides appears increasingly important and better elucidated in the biological properties of cell membranes. They act particularly as specific receptors in regard to biological macromolecules (hormones, virus, interferon, bacterial toxins, etc.) and thus allow them to express their respective beneficial or toxic messages for cells. This biological function of specific receptor makes possible numerous applications in the field of medicines and in the field of purifications by affinity chromatography.

It is known that gangliosides are glycolipids that can be isolated particularly in the brain, liver and kidneys, and whose molecule comprises particularly chemically combined fatty acids, sphingosine, oses and sialic acids. In particular, gangliosides have an N-acyl group (acyl derived from a fatty acid) and at least an N-acetyl group of a galactosamine.

According to the nomenclature proposed by Svennerholm, J. Neurochem., 10,613 (1963), the various gangliosides are designated by the letter G followed by one of four letters M, D, T or Q depending on whether the ganglioside is a mono-, di-, tri- or tetra sialoganglioside. These letters are followed by numerical indices making it possible to distinguish gangliosides containing the same amount of sialic acid but having different chromatographic mobilities. By analogy with the nomenclature proposed by Svennerholm for ganglioside $G_{M1}$ there will be designated below by "lysogangliosides" the products obtained by total hydrolysis of N-acetyl and N-acyl groups of gangliosides into $NH_2$ groups.

The various gangliosides, which can be used as starting products in this application, can be prepared, for example, by the methods already described, for example, by adsorption on an anion exchange resin followed by selective elution by a gradient of increasing concentration of potassium acetate in methanol; see Fredman and coll., Biochemia et Biophysica Acta (1980); see also the report of Fredman and coll., "Structure and Function of Gangliosides," Le Bischenberg Congress, Strasbourg, April 1079, published by Plenum Press.

If a given ganglioside is chemically fixed on the surface of a suitably chosen chromatographic support, there is then available a new chromatographic support having a specific affinity for the biological macromolecule or particle that naturally and selectively recognizes that gangloside selected.

It is then possible to purify or isolate an entire family of biological macromolecules having a great therapeutic interest and to immobilize particles (or cells) of which certain gangliosides are markers, to mark or isolate them.

Thus, on a support covered with ganglioside $G_{M1}$, it becomes possible to purify cholera toxin or thermolabile enterotoxies secreted by E. coli and other enterobacteria. After inactivation with formol or other known processes, it would then be possible to prepare the corresponding vaccines.

On a support covered with gangliosides $G_{D1a}$, $G_{D1b}$ or $G_{T1}$, it becomes possible to fix tetanus toxin and then purify it to prepare an antitetanus vaccine that is more purified and perhaps still more immunogenic than the present vaccine.

On a support covered with $G_{M2}$, it becomes possible to isolate and purify interferon that is now raising much hope in antiviral and antitumoral therapy.

For many years, numerous chromatographic supports and numerous chemical reactions have been developed to fix a ligand (molecule or receptor having specific recognition properties) on a support, particularly for use in affinity chromatography.

The chemical function generally necessary on a support are —OH alcohol, —$NH_2$ amine, —COOH carboxylic acid,

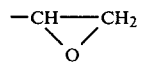

epoxy, —CH=O aldehyde functions.

The complementary chemical functions on the ligand are selected from the same functions according to known principles. The principles are described, for example, in the work "Affinity Chromatography, principles and methods," Pharmacia Fine Chemicals, Uppsala, Sweden (1974).

Two types of reactive chemical functions are naturally available in the particular case of gangliosides and glycolipids; there are actually numerous alcohol and often more than one carboxylic acid function carried by the neuraminic N-acetyl acid or other sialic acids. However, experience has shown that a fixing by these functions would destroy or make unusable the specific affinity properties expected from such a support.

The problem therefore is to bring out the other chemical functions on these gangliosides or glycolipids without destroying their biological activity.

Several methods developed by Uemura et al (1976) and Wiegandt et al (1970) consist in oxidizing the end portion of the sphingosine at the double bond to bring out a reactive function of the epoxy or aldehyde type.

However, these methods give only slightly usable results.

Another method, developed in 1963 by Taketomi et al, J of Biochim. 54,5,44 (1963) consists in transforming the gangliosides into lysogangliosides. The N-acetyl and N-acyl functions are totally hydrolyzed into an —$NH_2$ amino function by heating at 120° C. with reflux for 2 hours in a 10 N potash-butanol mixture (90:10). After extraction in an aqueous phase and concentration by evaporation, the resulting lysoganglioside can easily be coupled on various matrices. Thus, lysoganglioside $G_{M1}$ can be coupled to various polysaccharide supports to purify cholera toxin (see French patent application No. 77 28163).

However, when it was desired to apply the same method to fix gangliosides $G_{D1a}$, $G_{D1b}$ or $G_{T1}$, tetanus toxin receptors, it was not possible to make a support having an affinity for tetanus toxin, contrary to what was normally expected.

It has now been found that it is possible to transform gangliosides by managed hydrolysis into new "activated" ganglioside derivatives that do not have these drawbacks. The new derivatives have reactive groups making it possible to fix them on various supports in various ways without loss of their properties as ligands having specific affinity for biological macromolecules.

This method is applicable more generally to all gangliosides having several N-acyl groups. It should be made clear that, by convention, in this application the expression "ganglioside" takes in these various glycolipids.

Use of these supports in affinity chromatography has made it possible in the case of the $G_{D1b}$ or $G_{T1}$ derivative to purify tetanus toxin in only one step, showing that the new conditions of chemical activation of gangliosides respect their biological properties. A purification of this nature, so simple and so fast, has never been described as far as we know.

This process of managed activation of gangliosides was also successfully applied to the ganglioside $G_{M1}$ and to various other pure or mixed gangliosides.

This invention has as its object new ganglioside derivatives wherein they are products of partial deacylation of gangliosides, wherein they exhibit free amino groups that can be shown by a positive reaction in a ninhydrin test, wherein they are mobile in chromatography on a thin silica gel layer in the chloroformbutanol-water system (60:32:7) and wherein they exhibit the specific affinity properties of the gangliosides from which they are derived, said derivatives being able to be coupled to solid supports by amino groups that have appeared during partial deacylation, without loss of said specific affinity properties.

The invention also has as its object a process of preparing the new activated ganglioside derivatives.

According to this process, to activate the gangliosides chemically while retaining the essence of their biological properties, it suffices to treat them with an aqueous base solution at a temperature between 0° and 120° C., said temperature being lower the more basic the medium. For a final solution with an alkalinity comparable to normal potash or soda, 100° C. should not be exceeded. For an alkalinity comparable to decinormal potash or soda, 120° C. should not be exceeded. Most often, conditions are selected which make it possible to operate between 40° and 100° C.

The reaction time should be sufficient for free amino group to appear but, further, it should stop the reaction before total deacylation. The reaction time can easily be determined in each case by a simple test by using, for example, the ninhydrin test or the Sanger dinitrofluorobenzene test, by seeking an intermediate coloring less than that obtained after complete deacylation. Generally, the reaction time varies from 30 minutes to 24 hours.

The reaction solvent is either water or a mixture of water and organic solvents. Of the organic solvents there will be cited alcohols such as butanol.

Of the bases that can be used in the process of the invention, there will be cited those that can given a pH of 9 to 14 in water and in particular alkali metal hydroxides such as soda or potash.

It is simplest to dissolve the selected ganglioside in normal potash or soda and incubate this solution at a temperature of 60°–100° C. for about 2 hours.

The transformation is reflected by the appearance of at least an —NH$_2$ function resulting from partial hydrolysis of the N-acetyl or N-acyl function in sufficient number to allow fixing by the known methods by said —NH$_2$ function, but this transformation is rather limited to maintain the essence of the biological properties of the gangliosides selected.

It is possible to verify that these new basic hydrolysis conditions give a ganglioside very different from the lysoganglioside obtained by total hydrolysis under the conditions described by Taketomi. Actually, in thin-layer chromatography on silica gel in a chloroform-methanol-water system (60-32-7), the lysogangliosides obtained according to Taketomi absolutely do not migrate, whereas the gangliosides activated according to the present process give an Rf equal to or less than that of the corresponding natural ganglioside but always shifted in relation to the starting point.

As indicated above, the invention also has as its object new derivatives of partial deacylation of gangliosides coupled to solid supports by the amino groups that appeared during partial deacylation. The starting gangliosides are those cited above, and in particular the gangliosides $G_{D1a}$, $G_{D1b}$, $G_{T1}$ and $G_{M2}$.

For nonchromatographic applications particularly for biological tests, it is also possible to use other solid supports having absorbing properties, for example, polystyrene, polypropylene, latexes, etc., or able to fix a chemical coupling agent (dextran, cellulose, etc.) as will be set forth below.

The solid supports can also be solid supports that can be used in chromatography.

The invention also has as its object a process for obtaining the new ganglioside derivatives of the invention coupled to the supports.

This process, which comprises the stage of managed hydrolysis as described above, is characterized by the fact that it further comprises the stage consisting in fixing the activated ganglioside derivative by the amino groups, which have appeared, on a solid support by known methods.

The coupling reaction can be performed by known methods, as indicated above, in the presence possibly of an intermediate coupling agent (bifunctional derivative). Of the solid supports that can be used there will be cited porous solid supports. The porous solid supports are, for example, metal oxides such as silica, alumina, magnesia, etc., or their synthetic or natural derivatives such as glass, silicates, borosilicates, or kaolin, or organic polymers such as polysaccharides, vinyl polymers such as polyacrylics, polystyrenes, etc.

The porous inorganic supports can be supports modified to comprise reactive groups able to promote fixing of the new ganglioside derivatives by their amino groups that have appeared during partial deacylation. Said reactive groups can also be groups able to react with a function of a bifunctional derivative (coupling agent) whose other function is able to react with said NH$_2$ groups.

Reactive groups able to react with NH$_2$ groups are well known; they are particularly epoxy groups, carbonyl (particularly aldehyde) groups, carboxylic groups in the presence of carbodiimides, etc.

According to a particular embodiment, when the coupling is made with an epoxy type support or coupling agent, the epoxy type support and the managed hydrolysis and coupling reactions can be performed simultaneously by adding the support at the beginning or during hydrolysis reaction.

The ganglioside derivatives can be fixed, for example, on polysaccharide particles. Here the expression "polysaccharide" takes in modified polysaccharides. The polysaccharides are particularly dextran, cellulose, starch, agarose, etc., or again modified polysaccharides particularly dialkylaminoalkyl- or di(hydroxylalkyl) amino-alkyl-polysaccharides such as, for example, diethylaminoethyl dextran, diethylaminoethyl cellulose, etc.

The ganglioside derivative is fixed on polysaccharides with coupling agents such as diepoxides, dicarbonyls, epichlorohydrin or cyanogen bromide, by known methods.

Polysaccharides can also be used, not in the form of particles, but in the form of a coating on inorganic particles, particularly inorganic oxides such as those mentioned above.

Porous inorganic particles coated with polysaccharides or modified polysaccharides can particularly be those described in French patent application No 76.23176 or those described in French patent application No 77.28163.

The inorganic particles coated with polysaccharides, according to French patent application No 76.23176, consist of a porous inorganic support, such as a porous inorganic oxide coated directly on its surface with an amino polysaccharide polymer.

The porous inorganic support can be silica, alumina, magnesia, a titanium oxide, or their synthetic or natural derivatives such as glass, borosilicates, silicates, kaolin, etc.

The amino polysaccharide polymer is fixed on the porous inorganic support by gluing.

The internal surface of the porous inorganic support is, for example, less than or equal to 100 $m^2/g$ and if possible between 5 and 8 $m^2/g$. The average porous diameter is preferably greater than or equal to 25 nm and if possible between 50 and 1000 nm. For greater surfaces or small porous diameters the inside surface of the support becomes inaccessible to the polysaccharide polymer. The porous inorganic support is, for example, of silica or alumina and preferably a porous silica support having an anionic character obtained by the process described in French Pat. Nos. 1,473,239, 1,473,240, 1,475,929, 1,482,867 such as porous silicas sold by Rhone-Poulench Chimie Fine under the names SPHEROSIL XOB 030, XOB 015, XOB 005 and XOC 005.

The amino polysaccharide polymer that is used to impregnate and cover the inside surface of the porous inorganic support should have a pronounced cationic character and have good hydrophilic properties. It should have a molecular weight at least equal to $10^4$ daltons and if possible be between $10^5$ and $10^6$. It can have any formula and in particular can be an amino derivative of dextran, starch, cellulose, agarose or a natural or synthetic polymer of any known ose.

The amino functions of the polysaccharide polymer can be primary, secondary or tertiary and possibly quaternary.

The amino polysaccharide polymer can particularly correspond to the formula:

$$R\text{-}(CH_2)_n\text{-}NR_1(R_2)$$

wherein: R represents a polysaccharide residue such as, for example, a dextran, starch, cellulose or agarose residue, n is a whole number from 1 to 10 and preferably from 2 to 5, $R_1$ and $R_2$, identical or different, represent a lower alkyl or hydroxyalkyl radical, for example, the following radicals: $-CH_3$, $CH_2$, $-CH_3$, $-CH_2OH$, $-CH_2-CH_2OH$ or $CH_2-CHOH-CH_3$, these polymers being able to be quaternized with a standard quaternizing agent such as alkyl or hydroxyalkyl halides, dimethyl sulfate, etc.

Of the polymers of this type, there can be cited in particular the compounds known by the name DEAE DEXTRAN (diethylamino ethyl dextran) with a molecular weight of 500,000 and QAE DEXTRAN (quaternized diethylamino ethyl dextran) sold by the Pharmacia firm and the compound DEAE starch (diethylamino ethyl starch) and cationic starches such as those sold under the tradename CATO by the Roquette National company.

The amino polysaccharide polymer can also be crosslinked with a crosslinking agent, for example, a carbonyl compound, a diepoxide such as 1-4 butanedioldiglycidylether, or epichlorohydrin or epibromohydrin.

The ganglioside derivatives are fixed on porous supports thus coated, for example, with the coupling agents already mentioned above.

The porous inorganic particles, coated with modified or unmodified polysaccharides, according to French patent application No 77.28163, consist of a porous inorganic support coated with a polysaccharide polymer, or with a modified polysaccharide polymer, for example, an amino polysaccharide as mentioned above, said polysaccharide coating, if necessary, being stabilized by crosslinking, and a ganglioside derivative of the schematic formula $R''\text{-}NH_2$ being grafted on said polysaccharide or modified polysaccharide coating, $R''$ being the residue of the ganglioside derivative molecule, the grafting bond of said molecule answering to the formula $R_3\text{-}CH_2\text{-}NH\text{-}R''$, $R''$ being defined as above and $R_3\text{-}CH_3$-representing the residue of said polysaccharide or modified polysaccharide polymer when they have been subjected to an oxidizing cutting reaction followed by a hydrobromide reduction, for example.

The porous inorganic supports are those already indicated above; the polysaccharide polymer is particularly cellulose; the modified polysaccharide polymer is especially diethylaminoethylcellulose; the coating of the modified or unmodified polysaccharide polymer, if necessary, is stabilized by crosslinking, the crosslinking agent being such as those mentioned above.

The process of preparing these materials is characterized by the fact that the porous inorganic support is coated with the polysaccharide polymer or modified polysaccharide polymer, that, if desired, the polysaccharide coating is transformed into a modified polysaccharide coating, that, if necessary, crosslinking is performed to stabilize the coating, that said polysaccharide or modified polysaccharide polymer is subjected to an oxidizing cutting reaction by known methods, the resulting oxidation product is made to react with the activated ganglioside derivatives as defined above, of the schematic formula $R''\text{-}NH_2$, then that the resulting imino derivative is subjected to the action of a reducing agent able to reduce the imino bond to an amino bond.

The invention also has four its object application of the new products of partial deacylation of gangliosides to purification or isolation of biological macromolecules, particles or cells, or their elimination.

This application is characterized by the fact that a support on which is fixed the activated ganglioside or glycolipid derivative defined above is put in contact with a solution containing or able to contain the macromolecules or particles or cells it is desired to purify, isolate or eliminate. It will then be possible either to seek the presence of absence of the macromolecule (or particle or cell) on the support thus coated with the activated derivative (development according to known methods) or separate said macromolecule (or particle or cell) to isolate and purify it. Thus it is possible to fix tetanus toxin on a support coated with an activated derivative of ganglioside $G_{D1a}$ and/or $G_{D1b}$ and/or $G_{T1}$, to fix interferon on a support coated with activated derivative of ganglioside $G_{M2}$ and fix leukemia lymphocytes on a support coated with activated derivative of ganglioside $G_{M3}$.

According to a particular embodiment, this application is made by applying the methods of affinity chromatography. To do this, a column is made having a solid support on which is fixed an activated ganglioside derivative as defined above and a solution containing the macromolecules it is desired to isolate or purify is pass in said column. If necessary, the macromolecule to be isolated is eluted when it has been fixed on the ganglioside derivative.

If it is simply desired to eliminate an impurity by fixing this impurity on activated glycolipid, it obviously is not necessary to perform final elution.

On the other hand, if it is desired to obtain the product that has been selectively fixed on the activated glycolipid, the final elution should be performed.

According to a particular application of the invention, tetanus toxin is separated from a solution containing it in the following manner:

A column is made having a support on which is fixed activated ganglioside $G_{D1b}$ and/or $G_{T1}$, a solution containing the tetanus toxin is made to go over the column, and, if desired, the toxin is eluted in case it is desired to obtain a purified tetanus toxin.

The following examples illustrate the invention without, however, limiting it

EXAMPLE 1—Activation of ganglioside $G_{M1}$ 5 micromoles of $G_{M1}$ are dissolved in 1 ml of N soda and the solution is incubated at 80° C. for 2 hours. The solution can then be diluted and adjusted for coupling of the activated ganglioside according to any of the methods described below. The same method is applicable to other gangliosides such as $G_{D1b}$, $G_{T1}$, $G_{M2}$ and other glycolipids.

The resulting product shows a positive reaction in the ninhydrin test; the coloring observed, however, being less intense than that observed with lysoganglioside $G_{M1}$.

EXAMPLE 2—Activation of ganglioside $G_{M1}$ 10 micromoles of $G_{M1}$ are dissolved in 10 ml of N/10 soda and the solution is incubated at 40° C. for 15 hours. The solution is then ready for coupling of the activated ganglioside by any of the methods described below. The ninhydrin and Sanger tests are positive. In case of coupling on an epoxy support, this support can advantageously be added at the beginning of the alkaline treatment. Activation of the ganglioside and its fixing on a support are then done in the same stage at the same pH.

The same method is applicable to other gangliosides and glycolipids such as those mentioned above.

EXAMPLE 3—Activation of ganglioside $G_{D1b}$ 10 micromoles of $G_{D1b}$ are dissolved in 1 ml of N potash and the solution is incubated at 60° C. for 2 hours. The resulting solution, which gives a positive ninhydrin test, is then diluted and adjusted for coupling of the activated ganglioside by any of the methods described below.

The same method is applicable to other gangliosides and glycolipids.

EXAMPLE 4—Activation of ganglioside $G_{T1}$ 10 micromoles of $G_{T1}$ are put in suspension in 10 ml of 10 N butane-potash mixture (90:10); the suspension finally is equivalent to normal potash. After incubation for 2 hours at 60° C. and addition of an equal volume of water, the aqueous phase containing activated ganglioside, giving a positive ninhydrin test, is taken and adjusted for coupling of the activated ganglioside by any of the methods described below.

The same method is applicable to other gangliosides and glycolipids.

EXAMPLE 5—Activation of ganglioside $G_{D1b}$ 15 micromoles of $G_{D1b}$ are put in suspension in 10 ml of N butanol-potash solution (90:10). The final suspension is equivalent to decinormal potash. After incubation for 2 hours at 120° C. (with reflux) and addition of an equal volume of distilled water, the aqueous solution containing the activated ganglioside is taken and adjusted for coupling of the activated ganglioside by any of the methods described below. It shows a positive ninhydrin test.

The same method is applicable to other gangliosides and glycolipids.

EXAMPLE 6

Coupling of gangliosides thus activated on a polysaccharide matrix by a bifunctional agent having epoxy functions In all cases this coupling method leads to fixing the ganglioside by an extremely stable amino derived from the primary amino function that has appeared by managed hydrolysis, which makes it possible to obtain very long-lived supports.

6.1.—It is possible, for example, to use a product derived from agarose sold by Pharmacia (Uppsala, Sweden) under the name of "epoxy activated Sepharose 6B" and to perform the fixing according to the recommendations of the manufacturer. A dose of 1 to 10 mmole/ml is recommended. Determination of sialic acid before and after coupling makes it possible to verify the good fixing of the ligand.

6.2—It is possible to use other polysaccharides such as cellulose. Coupling with a diepoxy agent—for example, 1,4-butanedioldiglycidylether (Aldrich)—can be done by incubating 10 g of cellulose overnight in a mixture containing 20 ml of N NaOH, 20 ml of butanedioldiglycidylether and 40 mg of $NaBH_4$.

The next day the support is washed with alcohol, water and finally 0.1 N soda. After draining by filtering, the support is put in contact for a night with one of the previously activated gangliosides and in solution in 0.1 N soda. A dose of 1 to 10 mmole/ml is recommended. An incubation temperature of 20° to 40° C. is preferable.

6.3 Finally, it is also possible to use porous inorganic supports impregnated with polysaccharides such as those previously described in French patent 76.23176 and secondarily activated by the same diepoxide reagent. This support is particularly recommended for industrial applications.

EXAMPLE 7

Coupling of the gangliosides thus activated on a polysaccharide matrix oxidized by sodium periodate For this method, the cellulose or porous supports impregnated with polysaccharides such as those of French patent application No. 76.23176 are preferable. Actually, agarose is barely oxidized under the same conditions.

This method has already been applied (see French patent application 77.28163) for coupling of lysogangliosides prepared by the taketomi method.

The conditions for fixing the gangliosides activated according to the present process are identical.

To 10 g of support (for example, cellulose) are added 100 ml of 0.02 M sodium periodate for 2 hours at ambient temperature.

The support is then washed in an 0.02 M pH 9 sodium carbonate solution to which are added 10 g/l NaCl, drained by filtering and to which are added 15 ml of a solution of pH 9 of gangliosides activated according to any of examples 1 to 5 above. A dose of 1 to 10 mmole/ml of support is recommended.

After incubation overnight at ambient temperature, sodium hydrobromide NaBH$_4$ is added for 2 hours at 20° C. (0.2 M finally) to reduce the resulting imino bonds to extremely stable amino bonds. Here again, the resulting supports have an excellent life and can be reused dozens or hundreds of times.

EXAMPLE 8

Coupling of gangliosides thus activated on a polysaccharide matrix by the cyanogen bromide method The method is that described by Porath et al, Nature, 215, 1491 (1967). In practice, it suffices to mix the activated Sepharose with cyanogen bromide sold by Pharmacia (Uppsala, Sweden) with pH 11 according to instructions for use. A dose of 1 to 10 mmole of activated ganglioside per ml of gel again is recommended here. It is possible to adapt this technique to cellulose or the porous inorganic supports described above, without changing the operating conditions in any way.

EXAMPLE 9

Application to fixing and purifying tetanus toxin

By way of example, the results obtained on a porous inorganic support impregnated with polysaccharide according to a method already described in French patent application No. 76.23176 are described below. This support was chosen because it exhibits remarkable mechanical resistance properties, making it very useful for industrial purifications.

The porous inorganic support is silica such as that sold by Rhone-Poulenc under the name SPHEROSIL XOC 005. Its specific surface is about 10 m$^2$/g, its average porous diameter is about 300 nm. This silica is impregnated with a monomolecular layer of DEAE Dextran and crosslinked by a process already described in French patent application 76.23176. By applying the method described in one of examples 6 to 8 above, to 10 g of this support, it is possible, for example, to fix 50 micromoles of ganglioside $G_{D1b}$ or $G_{T1}$, previously activated according to this invention in examples 1, 2, 3, 4 or 5 above. To do this, 10 g of support are washed in an 0.1 N soda solution and put in a column. They occupy a volume of about 23 ml. The column is balanced in a solution containing glycocoll (20 g/l) and NaCl (10 g/l). A filtrate of Clostridium tetani culture containing, in the raw state, tetanus toxin titrating 500 units Lf/ml is dialyzed against this same buffer. 50 ml of this impure tetanus toxin solution are then filtered on this column. All the impurities not recognizing ganglioside $G_{D1b}$ or $G_{T1}$, go through the column, only the tetanus toxin is fixed on the column and can be recovered by elution with 0.1 N ammonia or a pH 9 buffer containing glycoll (20 g/l) and NaCl (60 g/l).

The recovered product contains about 70% of the biological activity present in the initial culture. With this single stage, the toxin reaches and even exceeds the standards already published (see B. Bizzini et al, Bull. Inst. Pasteur 72, 177, 1974). The toxin thus purified has an average specific activity of about 3500 lF/mg of nitrogen. The (D.O. 280 nm)/(D.O. 260 nm) ratio is equal to about 2. By immunodiffusion in gelose against a culture antifiltrate serum giving numerous precipitation lines with the initial culture filtrate, a single precipitation line is observed with the toxin thus purified. This line gives a reaction completely identical with a specific reference antitoxin serum or with a purified reference toxin supplied by the Pasteur Institute.

It should be noted that a support prepared in the same way with a ganglioside $G_{D1b}$ or $G_{T1}$, hydrolyzed under less gentle conditions described by Taketomi, article cited, does not allow any fixing of the tetanus toxin. It is not possible to fix the same unactivated ganglioside on a support prepared by the methods described above.

EXAMPLE 10

Application to fixing and purifying cholera toxin

The porous inorganic support is silica such as that sold by Rhone-Poulenc under the name SPHEROSIL XOC 005. Its specific surface is about 10 $m^2/g$, its porous diameter is about 300 nm; this silica is impregnated with a monomolecular layer of DEAE Dextran and crosslinked by the process described in French patent application No. 76.23176. By applying the method described in examples 6, 7 or 8 of this application to 1 g of this support, it is possible, for example, to fix 5 u moles of ganglioside $G_{M1}$ previously activated according to examples 1, 2, 3, 4 or 5 cited above.

This support is then washed with 0.1 N soda and put in a column. The column is balanced in a solution containing 0.05 M at pH7 of sodium citrate to which are added 10 g/l of NaCl. A culture filtrate of "Vibrio cholerae INABA 569 B" containing, in the raw state, 25 μg/ml of cholera toxin is dialyzed against the same buffer. 500 ml of this impure solution are then filtered on the column. All the impurities not recognizing ganglioside $G_{M1}$ go through the column. Only the cholera toxin is fixed and can be recovered by elution with 0.05 M pH 2.8 citric acid. The recovered product contains about 100% of the biological activity present in the initial culture. The cholera toxin thus purified (12.5 mg) appears to be identical with that prepared by the process discovered in French patent application No. 77.28163.

In the same way, fixing of ganglioside $G_{M1}$ is done by the same method on other supports from agarose or cellulose.

I claim:

1. A partially deacylated derivative of a ganglioside or glycolipid having an N-acyl group and being selected from $G_{D1a}$, $G_{D1b}$ and $G_{T1}$ gangliosides, said derivative exhibiting specific affinity properties when coupled to a solid support, wherein said derivative exhibits free amino groups that can be brought out by a positive reaction in the ninhydrin test, wherein also said derivative is mobile in chromatography on a thin silica gel layer in a 60:32:7 chloroform-methanol-water system, and wherein said derivative exhibits the specific affinity properties of the ganglioside or glycolipid from which it is derived, said derivative being capable of being coupled to a solid support by amino groups that have appeared during partial deacylation, without loss of said specific affinity properties.

2. The derivative of claim 1 wherein the ganglioside is ganglioside $G_{D1a}$.

3. The derivative of claim 1 wherein the ganglioside is ganglioside $G_{D1b}$.

4. The derivative of claim 1 wherein the ganglioside is ganglioside $G_{T1}$.

5. The derivative of claim 1 which is fixed on a solid organic or inorganic support.

6. The derivative of claim 5 wherein said support is a modified or unmodified organic polymer and wherein the ganglioside derivative is fixed on said support by amino groups that appeared during partial deacylation.

7. The derivative of claim 5 wherein said support is an inorganic porous body modified to make appear reactive groups capable of reacting with reactive groups of a coupling agent or with the $NH_2$ groups of said derivative.

* * * * *